United States Patent
Wu et al.

(10) Patent No.: US 10,281,369 B2
(45) Date of Patent: May 7, 2019

(54) DUAL-IMAGE BASED BIOIMAGING DEVICES AND TECHNIQUES

(71) Applicant: VOR, INC., San Diego, CA (US)

(72) Inventors: TsungFeng Wu, San Jose, CA (US); Yu-Chen Chen, San Diego, CA (US)

(73) Assignee: Vor, Inc., San Diego, CA (US)

( * ) Notice: Subject to any disclaimer, the term of this patent is extended or adjusted under 35 U.S.C. 154(b) by 0 days.

(21) Appl. No.: 16/065,677

(22) PCT Filed: Dec. 23, 2016

(86) PCT No.: PCT/US2016/068593
§ 371 (c)(1),
(2) Date: Jun. 22, 2018

(87) PCT Pub. No.: WO2017/112957
PCT Pub. Date: Jun. 29, 2017

(65) Prior Publication Data
US 2019/0017905 A1    Jan. 17, 2019

Related U.S. Application Data

(60) Provisional application No. 62/387,575, filed on Dec. 23, 2015.

(51) Int. Cl.
*G01N 1/00* (2006.01)
*G01N 21/00* (2006.01)
(Continued)

(52) U.S. Cl.
CPC .............. *G01N 1/10* (2013.01); *A61B 5/6898* (2013.01); *G01N 21/31* (2013.01); *G01N 21/47* (2013.01);
(Continued)

(58) Field of Classification Search
CPC ........ G01N 21/01; G01N 21/47; G01N 21/64; G01N 21/643; G01N 21/6486; B01L 2200/10; B01L 2300/168
See application file for complete search history.

(56) References Cited

U.S. PATENT DOCUMENTS

| | | | |
|---|---|---|---|
| 2005/0105077 A1* | 5/2005 | Padmanabhan .... | G01N 15/1484 356/39 |
| 2008/0181827 A1* | 7/2008 | Bassler ................ | G01N 15/147 422/119 |

(Continued)

OTHER PUBLICATIONS

Wu, T. et al., Label-free Optofluidic Cell Classifier Utilizing Support Vector Machines, Sep. 1, 2014, https://www.ncbi.nlm.nih.gov/pmc/articles/PMC3755465/pdllnihms497145.pdf.
(Continued)

*Primary Examiner* — Nathan A Bowers
(74) *Attorney, Agent, or Firm* — Perkins Coie LLP

(57) ABSTRACT

Disclosed are methods, systems, and devices for detecting biological analytes in a sample. The disclosed technology can be used to obtain readings of analyte concentration in a sample by imaging scattered light from an angled narrow beam illuminator. A fluid sample containing one or more biological, organic, and inorganic analytes including proteins, viruses, bacteria, phages, toxins, peptides, DNA, RNA, hormones, chemicals, drugs, and isotopes can be transferred to a microfluidic device having one or more channels with dimensions to generate capillary action for sample transport. The geometry of the microfluidic device may include a reservoir and sensing area, wherein an immunometric reaction can take place for the narrow beam scanning. The test particle may be coated with a specific binding member that is used to bind the binding pair member on an analyte in a sample. Test particles form the binding and the particle/analyte conjugate may be scanned.

4 Claims, 14 Drawing Sheets

(51) Int. Cl.
    *G01N 1/10*         (2006.01)
    *G01N 21/31*       (2006.01)
    *G01N 21/47*       (2006.01)
    *H01L 27/146*     (2006.01)
    *A61B 5/00*        (2006.01)
    *G01N 21/64*       (2006.01)
    *B01L 3/00*        (2006.01)

(52) U.S. Cl.
    CPC ....... *G01N 21/64* (2013.01); *H01L 27/14643* (2013.01); *B01L 3/502715* (2013.01); *B01L 3/502769* (2013.01)

(56) References Cited

U.S. PATENT DOCUMENTS

| | | |
|---|---|---|
| 2010/0245776 A1 | 9/2010 | Yamamoto |
| 2011/0157592 A1 | 6/2011 | Tsao et al. |
| 2013/0326941 A1* | 12/2013 | Pickett .................. A01G 7/045 47/1.4 |
| 2016/0238512 A1* | 8/2016 | Furuya ............... G01N 15/1436 |
| 2018/0003634 A1* | 1/2018 | Bo ......................... G01N 21/64 435/283.1 |

OTHER PUBLICATIONS

International Search Report and Written Opinion for PCT/US2016/068593, dated May 23, 2017 (10 pages).

\* cited by examiner

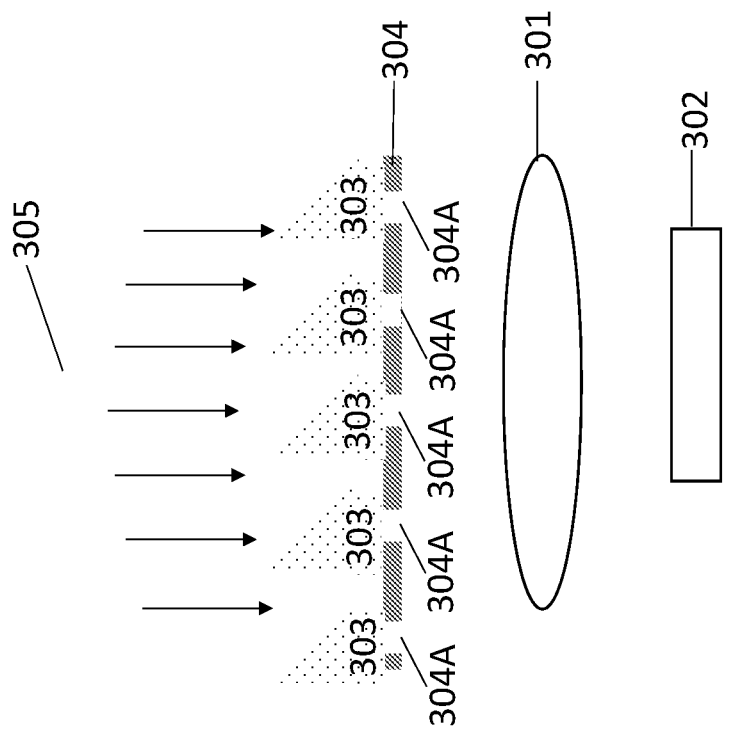

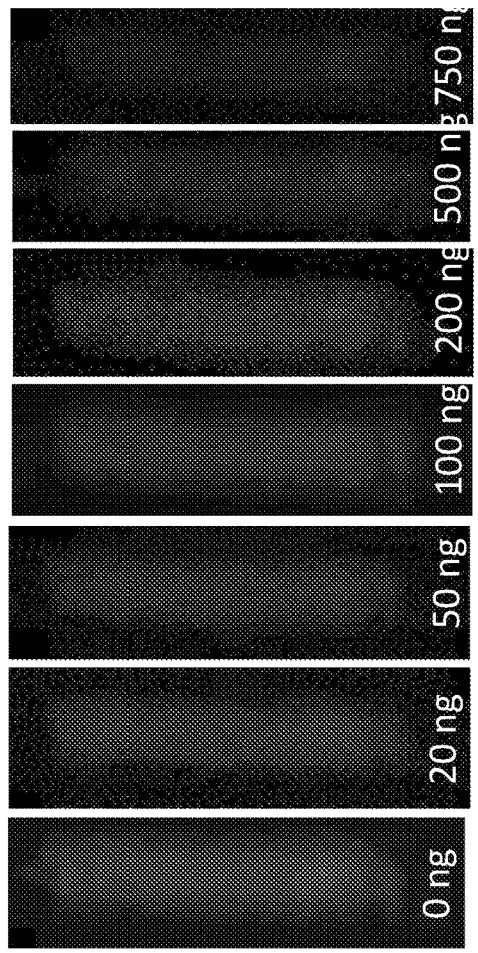
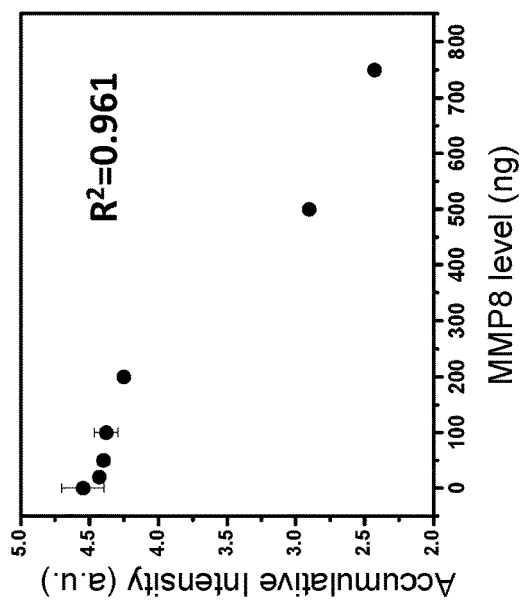
FIG. 7

DUAL-IMAGE BASED BIOIMAGING DEVICES AND TECHNIQUES

CROSS-REFERENCE TO RELATED APPLICATION

This patent document claims the priority and benefits of U.S. Provisional Application No. 62/387,575, filed on Dec. 23, 2015, and entitled "FLUORESCENT-FREE BIOIMAGING." The entire content of the before-mentioned patent application is incorporated by reference as part of the disclosure of this document.

TECHNICAL FIELD

This patent document relates to systems, devices, and processes that use fluorescent-free imaging and biosensing technologies.

BACKGROUND

Imaging of biological substances in form of particles in fluids has important applications in medical and biological applications. Various imaging devices for such applications use specially designed imaging systems to interface with microfluidic platforms.

SUMMARY

Apparatuses, systems, methods, and computer-readable media are disclosed. In some example embodiments, a bioimaging apparatus may include a microfluidic holder that holds a microfluidic device to carry a fluid to be measured. The apparatus may further include an optically opaque plate formed on a first side of the microfluidic holder and structured to include one or more slits to allow passage of light, and/or an illumination light source structure to produce at a predetermined angle illumination light towards the optically opaque plate to pass through one or more slits as a directional illumination beam to enter the microfluidic device to illuminate the fluid. A fluorescent material may be placed adjacent to the optically opaque plate at a location to be illuminated by the illumination light to produce fluorescent light that passes through the one or more slits to enter the microfluidic device to illuminate the fluid. An image capture plate may be placed on a second side of the microfluidic holder and structured to block the illumination light that transmits through the microfluidic device at the predetermined angle and to include an imaging aperture that allows transmission of a portion of scattered light from the fluid caused by illumination of the fluid by the illumination light and a portion of the fluorescent light that passes through the fluid which projects a shadow created by a particle in the fluid passing through the imaging aperture when illuminated by the fluorescent light.

In another aspect, a method is disclosed including illuminating, by an incident light source, a target at a predetermined angle through one or more slits, wherein the one or more slits restrict the incident to a narrow beam. The method may further include illuminating, by the incident light source, an autofluorescent layer to generate an autofluorescent light source. The method may also include imaging, by an imager, a first portion of scattered light from the target, wherein the first portion of scattered light is the incident light source scattered by the target, wherein the imager is positioned to capture the first portion of scattered light and positioned to capture a second portion of the autofluorescent light source passing past the target, wherein the target generates a shadow on the imager from autofluorescent light source being blocked by the target, and wherein the predetermined angle causes incident light source not scattered by the target to be blocked from the imager.

In other example embodiments, a bioimaging device may include a light source configured to emit an incident light and a dual-vision imaging field. The dual-vision imaging field may include a beam narrower structure, which contains at least one substrate layer, fabricated to form one or more slits, and an autofluorescent layer disposed on a surface of the at least one substrate layer and/or covering the one or more slits. The beam narrower structure may be configured to generate a narrow beam of light from the incident light emitted by the light source by tilting the incident light through the one or more slits. The bioimaging device may further include a microfluidic device including channels for receiving a sample fluid that includes target particles, each channel including an imaging region illuminated by the narrow beam of light to illuminate the target particles in the sample fluid to generate scattered light from the target particles.

The bioimaging device may include any of the following features or in any feasible combination. The one or more slits on the at least one substrate layer may be arranged off-center from one or more slits on another substrate layer to tilt the incident light. The generated scattered light may represent a scattered light image of the target particles. The scattered light image of the target particles may include a dark-field scattering image. The autofluorescent layer may be configured to absorb a predetermined wavelength from the incident light passing through the one or more slits to generate autofluorescence, and/or a bright-field imaging region in each channel may be illuminated by the autofluorescence to illuminate the target particles in the imaging region. A transmissive image of the target particles may include a bright-field transmissive image. The one or more slits may have a width ranging from 2 microns to 20 microns, or 5 microns to 40 microns, or 1 micron to 5 microns, or 3 microns to 4 microns, or from 3 microns to 10 microns. The light source may be configured to introduce the incident light at an angle to generate an angled narrow beam. The light source may include a light emitting diode. A horizontal distance between two of the one or more slits may cause a predetermined width of the narrow beam. The autofluorescent layer may include a photoresist polymer. The autofluorescent layer may be disposed to form a shape over the one or more slits to alter a path of the incident light. The shape of the autofluorescent layer may include a micro pyramid shape. The shape of the autofluorescent layer may include a micro semi-pyramid shape. The autofluorescent layer may be shaped to convert the incident light into a narrow beam that illuminates at least one of the target particles to produce scattered light indicative of a dark-field image of the illuminated particle. The autofluorescent layer may be configured to produce fluorescence from the incident light, wherein the fluorescence illuminates at least one other target particle in the imaging region to generate a fluorescent transmissive light indicative of a bright-field image. A transmissive light image of the target particles may include a bright-field transmissive image. The microfluidic device may include a capillary-driven microfluidic device. The microfluidic device may be sized to be from ten microns to a few hundred microns. The microfluidic device may include multiple layers. The multiple layers of the microfluidic device may include a top layer including at least one sample introduction inlet and at least one outlet, a middle layer including the microfluidic channels, and a bottom layer including a reservoir pattern for enabling the target particles to undergo a specific binding reaction. The channels of the microfluidic device may be disposed to be parallel to one another and perpendicularly underlay respective slits to enable a multiplexed detection. Each microfluidic channel may be loaded with binding member coated particles for multi-sample detection.

In another aspect, there is a mobile bioimaging system. The bioimaging system may include a bioimaging device including a light source configured to emit an incident light and a dual-vision imaging field. The dual-vision imaging field may include a beam narrower structure, which contains at least one substrate layer, each fabricated to form one or more slits, and an autofluorescent layer disposed on a surface of the at least one substrate layer and/or covering the one or more slits. The beam narrower structure may be configured to generate a narrow beam of light from the incident light emitted by the light source by tilting the incident light through the one or more slits. The mobile bioimaging system may further include a microfluidic device including channels for receiving a sample fluid that includes target particles, each channel including an imaging region illuminated by the narrow beam of light to illuminate the target particles in the sample fluid to generate scattered light from the target particles, and/or an imager configured to capture the scattered light and generate a scattered light image based on the captured scattered light.

The bioimaging system may include any of the following features or in any feasible combination. The image may include a complementary metal oxide semiconductor (CMOS) imager. The CMOS imager may include a mobile device. The mobile device may include a smartphone. The bioimaging system may further include an external lens disposed between the bioimaging device and the imager. The bioimaging device may be configured to light signals indicative of both a bright field transmissive image and a dark field scattering image, and wherein the image is configured to capture the light signals to observe both the bright field transmissive image and the dark field scattering image within the same field of view on the imager. The microfluidic device may include a capillary-driven microfluidic device. The microfluidic device may be sized to be from 10 microns to a few hundred microns. The microfluidic device may include multiple layers. The multiple layers may include a top layer including at least one sample introduction inlet and at least one outlet, a middle layer including the microfluidic channels, and/or a bottom layer including a reservoir pattern for enabling the target particles to undergo a specific binding reaction. The channels of the microfluidic device may be disposed to be parallel to one another and perpendicularly underlay respective slits to enable a multiplexed detection simultaneously. Each microfluidic channel may be loaded with binding member coated particles for multi-sample detection.

BRIEF DESCRIPTION OF THE DRAWINGS

FIG. 3 illustrates an example of a structure including an array of pyramids, in accordance with some example embodiments;

FIG. 7 illustrates an example agglutination test, in accordance with some example embodiments;

Where possible, like reference numbers refer to the same or similar structures.

DETAILED DESCRIPTION

Figure 1A:
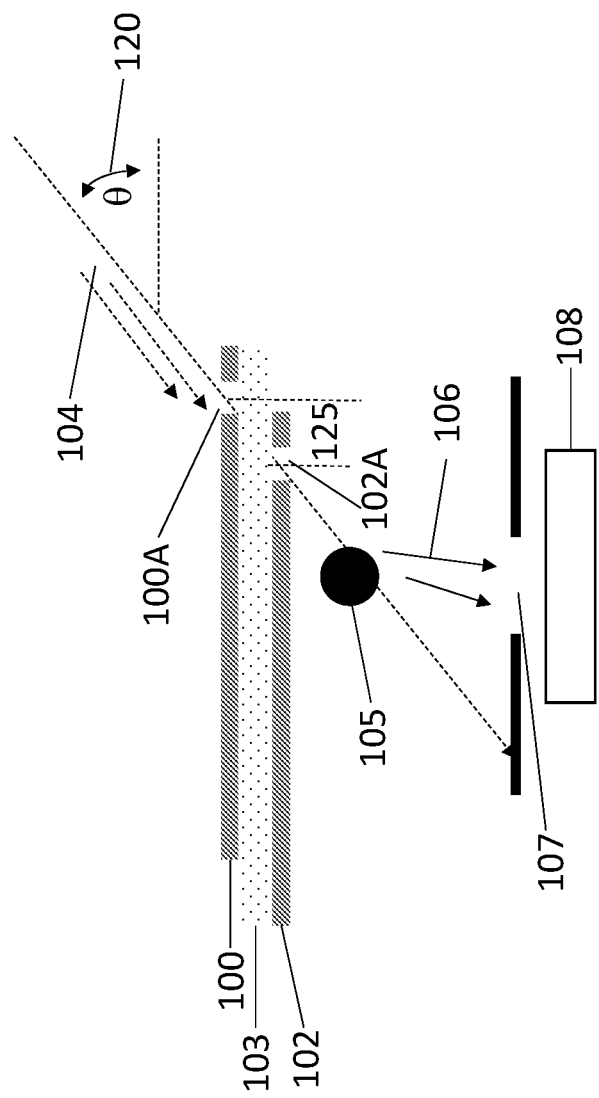
FIG. 1A illustrates an example of a slit to create a tilted narrow beam light source for particle detection, in accordance with some example embodiments.

The imaging techniques disclosed here use a dual-imaging approach to capture two different images of the sample to improve the imaging reliability and performance. In various applications of the disclosed dual-imaging approach, the imaging sensing module can be implemented using an existing imaging sensor in a device such as the CMOS sensor in a camera of a mobile devices such as a smart phone, without using a specially designed imaging sensing module dedicated to the bioimaging application only.

Mobile electronics including smartphones, tablets, etc. are equipped with various sensors, wireless connectivity, and processing capabilities. These devices allow users to perform a number of different operations and tasks related to work and entertainment. In the last few years, research has focused on the development of advanced smartphone-based devices and applications that offer cost-effective mobile healthcare to overcome constraints of time and place. Mobile devices provide an effective means of delivering mobile healthcare to remote, resource-limited, private and public settings. The real-time outcomes of diagnostics with information provided by mobile devices can be stored on a secure cloud server and be accessible by physicians from remote locations. This provides timely treatment via telemedicine. Even though the features of smartphones have significantly improved including more sophisticated sensors, biological detection is still unavailable.

One reason biological detection is still unavailable is that sensors, especially CMOS cameras on smartphones, are not sensitive enough to generate signals of sufficient quality from traditionally bioanalytical immunoassays using fluorescent-based methods. Narrow beam technology may leverage the refractive index difference between beads and a medium to produce detectable scattered light for imagers such as a complementary metal oxide semiconductor (CMOS) imager or any other type of imager. Without using expensive fluorescent molecules and complex sample preparation protocols, narrow beam scanning can offer real-time detection, one-step reaction protocol that is implemented on a smartphone-based platform.

Examples of implementations of the disclosed technology can be used to provide techniques, systems, and devices for simultaneously forming a dual-vision imaging field on CMOS imagers for quantitatively sensing the presence of analytes in a fluid sample. The disclosed technology can be implemented without requiring fluorescent-based imaging techniques. The disclosed dual-vision imaging technique can accommodate bright-field and dark-field images within the dynamic range of CMOS imagers. The disclosed technology can be implemented to detect biological, organic, and inorganic analytes such as bacteria, pathogens and/or their toxins, proteins, phages, viruses, peptides, DNA, RNA, hormones, chemicals, drugs, isotopes, or other biomolecules by binding a binding-member-coated particle to a binding pair member. The binding member refers to a molecule such as antibody, which produces a signal by binding to a site on a target analyte, which means the binding pair member.

In one aspect, the disclosed technology can be implemented in various ways to introduce a tilting light beam to detect the analytes with high sensitivity and high specificity in very short time duration by conjugating the binding member to a binding pair member of analyte.

In another aspect, the disclosed technology can be implemented in various ways to produce dual-vision imaging on CMOS imagers of mobile devices.

In yet another aspect, the disclosed technology can be implemented to utilize capillary-driven microfluidics to simplify the ease of use for biological analyte detection as a lab-on-a-chip device.

The disclosed technology may provide a system that introduces a tilting narrow beam for the detection of analytes on a CMOS imager (e.g., on a mobile device) cost-effectively by utilizing the binding chemistry of a binding member against a binding pair member of analytes. For example, analytes such as bacteria contain at least one binding pair member that can bind with a binding member such as an antibody that is immobilized on the surface of the particle. The biochemical reaction provides versatile immunoassays. The disclosed technology can be implemented in ways that empower a wide range of immunoassays such as competitive homogeneous immunoassays, competitive heterogeneous immunoassay, one-site noncompetitive immunoassays, two-site noncompetitive immunoassays, and sandwiched noncompetitive immunoassays to be effectively and low-cost quantitative detection.

One of embodiments is to convert the qualitative immunoagglutination approach for rapid bacteria level classification. When the binding chemistry between the binding pair member of bacteria and the antibody of the particles occurs, more than one particle will capture the same bacteria to form the agglutination of particles, wherein the degree of particle agglutination depends on the concentration of bacteria in the sample The disclosed technology can be used to detect the presence of bacteria by collecting the scattered light of the particle agglutination that binds with the binding member and the binding pair member of bacteria, which is recorded in a dark-field imaging band. To observe features of particle agglutination, the disclosed technology uses the same CMOS imager to delineate the overall agglutination contour in a bright-field imaging band. To overcome the orders of magnitude of intensity difference beyond the dynamic range of a CMOS imager, the disclosed technology develops techniques to retain the intensity and contrast of both the bright-field transmissive image and the dark-field scattering image that are recorded in two regimes of the same CMOS imager.

In some implementations, the dark-field large-angle scattering image of the particle agglutination was obtained using an integrated micro pyramid with a slit to produce an equivalent of a narrow beam that slices through the flowing particle agglutination. The bright-field transmissive image can be produced by the autofluorescence of the material excited by the UV component of a white LED lamp while blocking the primary beam from reaching the CMOS imager. The overall device is extremely simple to construct and operate, consisting of an LED lamp, at least one patterned slits, and a low-cost magnification lens and an aperture in front of a commodity CMOS camera found in mobile devices.

After passing through the narrow slits, the LED light forms a narrow beam scanning through the samples flowing underneath. Depending on the format of immunoassays, the binding member coated particles can be flowing in the fluid sample (immunoagglutination format) within a microchannel or moving with the entire sliding microchannel substrate (conventional immunometric sandwich format). The primary titling narrow beam travelling through the particle/analyte conjugates cannot reach the CMOS sensor, and in some example embodiments only a small fraction of light scattered by the particle/analyte conjugates at a specific angle can reach the CMOS sensor and form the dark-field scattering image of the portion of the cell being illuminated by the narrow beam. After the entire particle/analyte conjugates cross the narrow beam sensing area, the scattering image of the full particle/analyte conjugates can be recorded. Because the large angle scattering may be dominated by Mie scattering governed by the contrast of the refractive index and the size of the object, the particle contributes most to the scattering image, offering high sensitivity for analyte detection. From the dark-field scattering patterns interrogated by the narrow beam, the accumulative and/or differential scattering intensity can be used as an indicator for the concentration of analytes with high contrast and spatial resolution. The disclosed technology can also create the bright-field transmissive image of the same particle/analyte conjugate after a preset time delay in a location that is at a distance from the dark-field scattering image. The acquisition of the bright field transmissive image that delineates the particle/analyte conjugate following the dark-field scattering image allows for real-time verification of true positive detection (whether from particle/analyte conjugate or from dust particles). For example, in fluid samples, debris or dust particles may be present that can produce similar scattering intensity or patterns in the dark-field scattering band. These unwanted impurities might be in from tens to hundreds of microns. The additional bright-field transmissive field can directly delineate the shape of these impurities, enabling execution of an image tuning process. With this alternatively debugging process, the disclosed technology can be implemented in specific ways that reduce or minimize false events to achieve high accuracy. The dual-vision imaging enables the recording of scattered light from the particle/analyte conjugate at multiple areas under the same field of view to allow the multiplex detection.

The disclosed technology can be used to detect analytes by offering a technology capable of titling and narrowing light beam to simultaneously form dual-vision images on the same CMOS imager, a capillary-driven microfluidic device capable of driving fluid analyte sample with a controlled flow rate to enable the binding chemistry between the binding pair member of analyte and the binding member immobilized on particle surface, wherein at least one binding pair member is able to bind to the antibody to form the binding complex and the formation of said particle/analyte conjugates produces the signal, and an immunoassay process comprising a number of specific particle-to-analyte binding due to binding complex reaction, wherein said the dark-field scattering image intensity detected by the disclosed technology is determined by the concentration of analytes.

Healthcare applications on mobile platforms is desirable due to the popularity of mobile devices, such as smartphones that also include sensors, wireless connectivity, and processing power. For example, CMOS imagers that are present in almost all mobile devices can be utilized for mobile healthcare applications because the detection of analytes by binding a binding member to a binding pair member (e.g. detection of bacteria such as an antigen by an antibody, or detection of an antibody in blood by another antibody; or binding of a chemical toxin to its epitope) reveals significant health and disease information. The disclosed technology provides techniques for high-quality detection results in a mobile platform that does not require sophisticated fluorescent labeling equipment and knowledge. Fluorescence-based cytometers and/or surface plasmon resonance (SPR) systems may detect and readout signals on a benchtop platform or on a mobile platform, such as a smartphone in a point-of-care and home diagnostic setting. The disclosed technology uses existing CMOS imagers in mobile devices without incorporating the sophisticated fluid control devices, lasers, photomultiplier tube (PMT) detectors, and optics required by flow cytometers, nor the high-power microscope and the associated light sources and detection devices for image-based cytometers. By eliminating these sophisticated devices, a user of a mobile device does not need the specialized knowledge and skills, or the auxiliary devices to stain or label the samples. Without staining, the images from image-based cytometers may lack the contrast for pathology and histology analyses. The disclosed technology using a CMOS imager in a mobile device offers an innovative approach to utilize a tilted incident light beam as an optical source and to collect the scattered light for detection of analytes to produce high-quality detection results fully compatible with CMOS imagers in mobile devices.

The disclosed technology can be used to obtain the quantitative and qualitative readings of analyte concentration in a sample with imaging scattered light by tilting a narrow beam. A fluid sample suspension may contain one or more analytes, such as viruses, bacteria, phages, toxins, proteins, peptides, DNA, RNA, hormones, chemicals, drugs, and isotopes, and may be transferred to a microfluidic device that has one or more channels with proper dimensions to generate capillary action for sample transport. The geometry of the microfluidic device may be is designed to include a reaction chamber for an immunoassay and a sensing area, wherein test particles are allowed to react with analytes in the reaction chamber. In some example embodiments, the surface of the test particle is coated with one or more of specific binding members that are used to bind the binding pair members on analytes in a sample. Once the analytes such as proteins, viruses, chemicals, and bacteria in a sample enter the reservoir region, one or more test particles form the conjugates with the analytes. Depending on the formats of immunoassay applied, the tilted incident narrow optical beam will produce scattered light from the particle/analyte conjugates, followed by imaging onto a CMOS imager. Using the disclosed technology, one or more biological analyte concentrations in a sample can be simultaneously measured on a capillary-driven microfluidic device without using conventional fluorescent labeling techniques.

In the disclosed technology, the specific binding pair member of analytes may interact with the binding member (e.g. antibody) coated on the surface of particle. The receptor-ligand interaction may form particle/analyte conjugates and produce the scattering signals. The scattered light can be imaged in the dark-field band and further examined in the bright-field transmissive imaging region on the CMOS imager.

In some example embodiments, the disclosed subject matter enables an imager with a limited dynamic range of usable light intensities to capture scattered light from a target particle and a shadow of the target particle created by the target particle blocking light from an autofluorescent source. For example, an incident light may be aimed so that a direct path of the incident light does not reach the imager but light scattered off the target particle in one position is received by the imager. In some example embodiments, the scattered light reaching the imager may be of lower intensity than the direct illumination. The incident light may further pass through an autofluorescent layer causing an autofluorescent light to be generated. The autofluorescent light may illuminate the target particle at a second position of the target particle where the target particle may generate a shadow on the imager due to the target particle blocking the autofluorescent light when the particle is at the second position.

FIGS. 1A-3 show example embodiments of a tilted narrow beam apparatus with a dual-vision dark-field scattering image and a bright-field transmissive image of particles on a CMOS imager.

FIG. 1A depicts an example embodiment of the disclosed technology that uses a slit of a few microns to create a narrow beam by either tilting the incident light, or placing an optical component such as lens on the top of the slit prior to introducing the incident light source, or a combination of tilting and a lens. For example, the slit may have a width of between 10 microns and 200 microns. Other slit widths may also be used. FIG. 1 shows an exemplary sandwich structure that includes two slit layers 100 and 102, and autofluorescent material 103 between slit layers 100 and 102. Slit layers 100 and 102 may also be referred to herein as substrate layers. A portion of the tilted or angled light from light source 104, may pass through slit layers 100 and 102 to illuminate particle 105. Light 104 may be incident on slit layers 100 and 102 at angle 120 of θ. Illuminated particle 105 may scatter some of the incident light 104 to produce scattered light 106 from particle 105. Scattered light 106 may be received by imager 108 that may be included in a portable device such as a smartphone. Imager 108 may be a CMOS imaging device or any other type of imaging device. In some example embodiments, orifice 107 can be used over imager 108 to form a dark-field scattering image. In some example embodiments, In some example embodiments consistent with FIGS. 1A and 1B, autofluorescent material 103 may absorb a portion of light 104 at one or more wavelengths, and may fluoresce to produce another light source 109. In a predetermined timeframe, particle 105 can reach the bright-field transmissive imaging region under illumination by fluorescence 109. The formation of a bright-field image can also be detected by imager 108 used in the dark-field scattering imaging.

In one aspect, slits 100A and 102A can be fabricated by using lift-off process to form a patterned metal film on the slit layers 100 and 102. The dimensions of slits 100A and 102A can be between approximately 10 microns and 200 microns wide, fabricated using a lithography method that may use a photoresist as a mold to transfer a designed pattern from a mask. In some implementations, the width of the slits such as slits 100A and 102A, can be between 2 microns and 20 microns, between 5 microns and 100 microns, between 75 microns and 150 microns, between 100 microns and 200 microns, between 10 microns and 200 microns, and/or between 3 microns and 10 microns. The dimensions and geometry of the microchannel underlying slit layer 102 can be designed such that particles 105 of a predetermined range of size can be illuminated within a predetermined time. The incident light 104 can be introduced at a predetermined angle 120 to form a tilted narrow beam. For example, the predetermined angle may be between 20 degrees and 60 degrees. Other angles may also be used. The light source can be incoherent such as light from an LED that may pass through the slits 100A and 102A without causing diffraction. Autofluorescent material 103 may be between slit layers 100 and 102. The autofluorescent material 103 may be applied by spinning a photoresist polymer onto a substrate, followed by curing with light or heat. Slits 100A and 102A may be offset by distance 125 to tailor the light beam width and/or accommodate angle 120 and slits 100A and 102A. In some example embodiments, the beam width of the narrow beam can be between microns and 4 microns, between 1 microns and 6 microns, between 5 microns and 20 microns, between 10 microns and 50 microns, between 30 microns and 80 microns, between 50 microns and 100 microns, and/or between 1 micron and 100 microns.

Figure 1B:
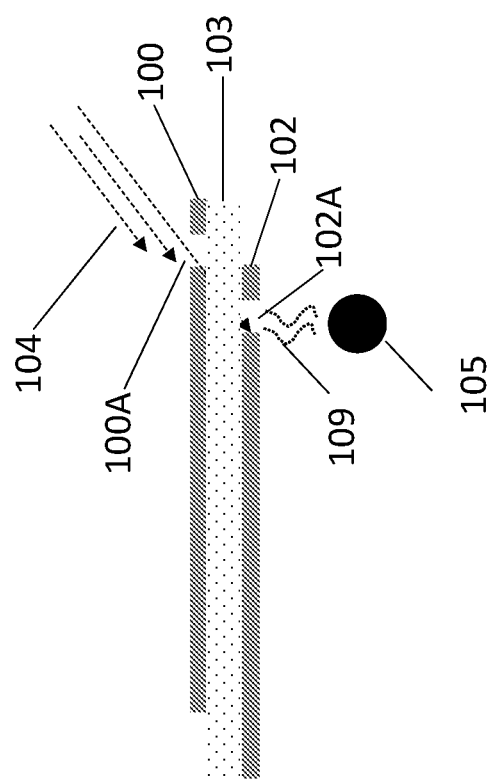
FIG. 1B illustrates an example of a sandwich slit to create a tilted narrow beam light source and autofluorescence for particle detection, in accordance with some example embodiments.
Figure 1C:
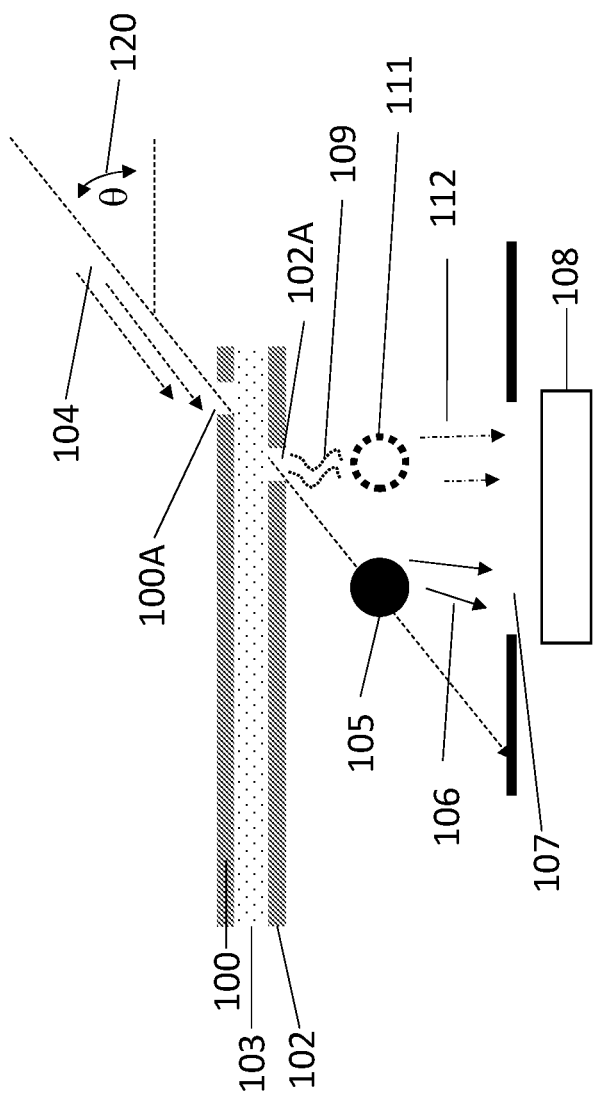
FIG. 1C illustrates another example of a sandwich slit to create a tilted narrow beam light source and autofluorescence for particle detection, in accordance with some example embodiments.

In an embodiment consistent with FIG. 1C, slits 100A and 102A can be fabricated by using lift-off process to form a patterned metal film on the slit layers 100 and 102. The dimensions and geometry of the microchannel underlying slit layer 102 can be designed such that particles 105 of a predetermined range of size can be illuminated within a predetermined time. The incident light 104 can be introduced at a predetermined angle 120 to form a tilted narrow beam. The angle 120 can be between 20 degrees and 60 degrees, between 10 degrees and 30 degrees, between 40 degrees and 70 degrees, and/or between 50 degrees and 80 degrees. The light source can be incoherent such as light from an LED that may pass through the slits 100A and 102A without causing diffraction. Autofluorescent material 103 may be between slit layers 100 and 102. The autofluorescent material 103 may be applied by spinning a photoresist polymer onto a substrate, followed by curing with light or heat. Slits 100A and 102A may be offset by distance 125 to tailor the light beam width and/or accommodate angle 120 and slits 100A and 102A. In some embodiments, the beam width of the narrow beam can be between 3 microns and 4 microns, between 1 micron and 6 microns, between 5 microns and 20 microns, between 10 microns and 50 microns, between 30 microns and 80 microns, between 50 microns and 100 microns, and/or between 1 micron and 100 microns. A portion of the tilted or angled light from light source 104, may pass through slit layers 100 and 102 to illuminate particle 105. Illuminated particle 105 may scatter some of the incident light 104 to produce scattered light 106 from particle 105. Scattered light 106 may be received by imager 108 that may be included in a portable device such as a smartphone. Imager 108 may be a CMOS imaging device or any other type of imaging device. The autofluorescent material 103 will form another light source 109 for transmissive imaging. Within preset delay, the same particle 105 will flow to the position 111 where autofluorescent light 109 will illuminate particle 105 and form image 112 in bright-field transmissive band received on imager 108. In some example embodiments, image 112 may include a shadow of particle 105. For example, particle 105 in position 111 may block light 109 thereby casting a shadow of particle 105 on imager 108.

In accordance with some example embodiments, FIG. 1A depicts scattering of incident light 104 by particle 105 (and does not show autofluorescent light from layer 103). FIG. 1B depicts autofluorescent light 109 impinging on particle 105 (and does not show scattered light). FIG. 1C depicts particle 105 at one time when in position to generate scattered light 106 from incident light 104, and particle 105 at position 111 when in position to be illuminated by autofluorescent light 109. In some example embodiments, when particle 105 is in position 111, particle 105 may generate a shadow on imager 108 due to autofluorescent light 109 that is blocked by particle 105 in position 111.

Figure 1D:
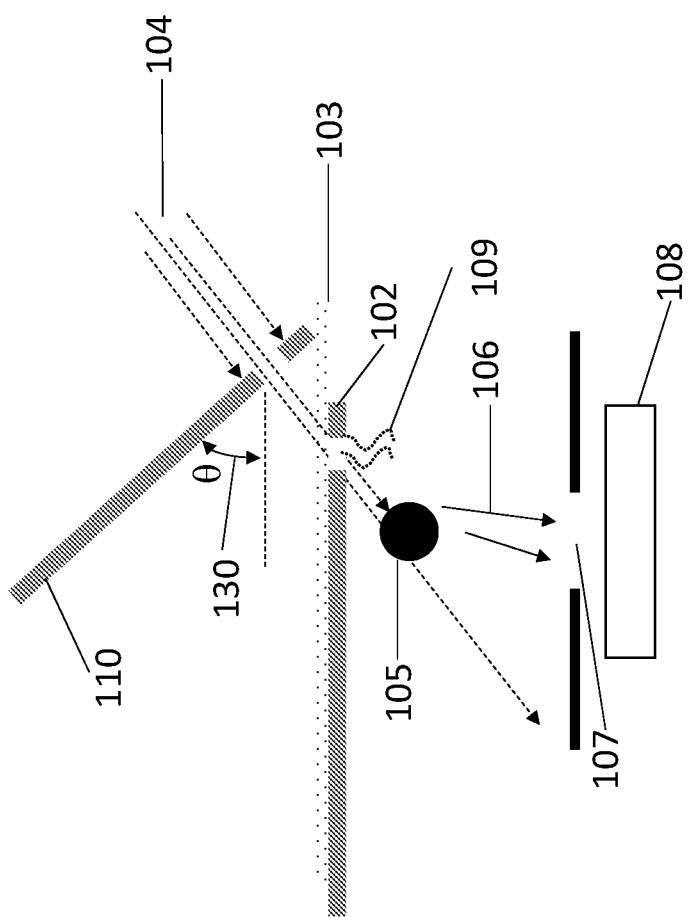
FIG. 1D illustrates another example of a tilted slit structure to create a tilted narrow beam light source and autofluorescence for particle detection, in accordance with some example embodiments.

In an embodiment consistent with FIG. 1D, slit layer 110 can be tilted by angle 130 to produce light 104. Tilted slit layer 110 may block incident light except light incoming at an angle approximately normal to angle 130. With single slit layer 102, the width and tilting angle 130 of slit 110 may determine a narrow beam width incident on particle 105. In some example embodiments, tilted slit layer 110 may be in close proximity to the autofluorescent material 103 to avoid diffraction that could widen the width of the narrow beam. In some example embodiments, the beam width of the narrow beam can be between 3 microns and 4 microns, between 1 micron and 6 microns, between 5 microns and 20 microns, between 10 microns and 50 microns, between 30 microns and 80 microns, between 50 microns and 100 microns, and/or between 1 micron and 100 microns.

Figure 2A:
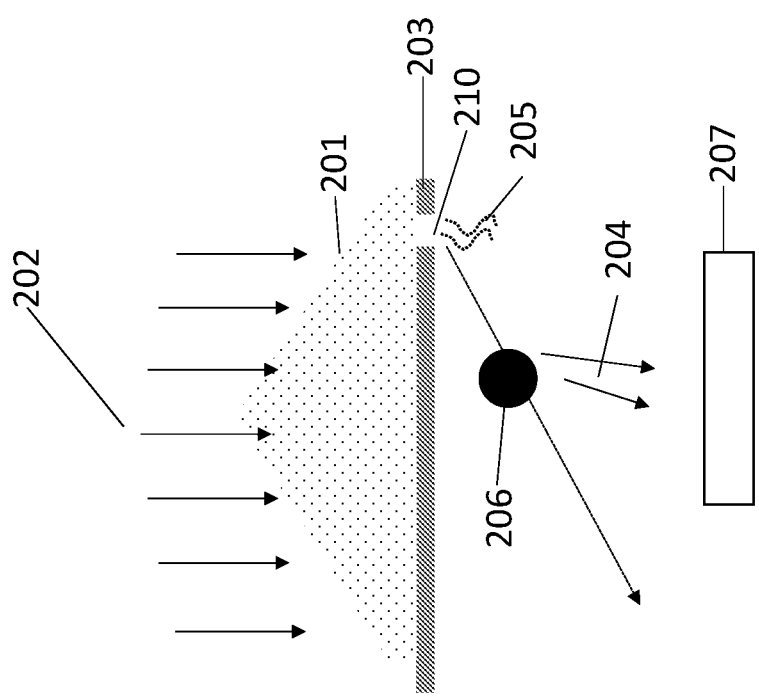
FIG. 2A illustrates an example of a pyramid structure, in accordance with some example embodiments.
Figure 2B:
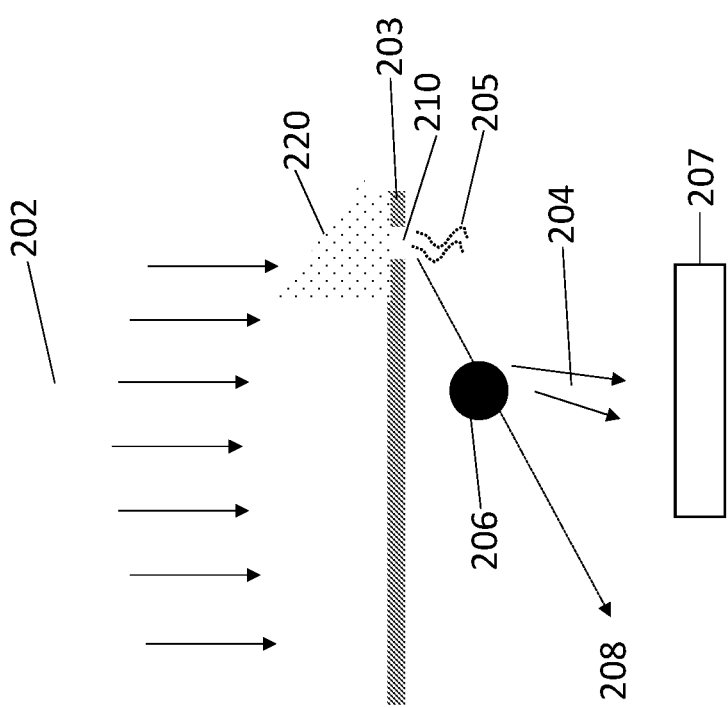
FIG. 2B illustrates an example of a semi-pyramid structure, in accordance with some example embodiments.

FIGS. 2A and 2B show exemplary micro pyramid 201, in accordance with some example embodiments. Micro pyramid 201 may include photoresist formed over slit layer 203 and slit 210. Micro pyramid 201 may change by refraction the path of incident light 202 that passes through slit 210. For example, photoresist in micro pyramid 201 may alter the path of incident light via refraction similar to a lens. Micro pyramid 201 may include a an autofluorescence material that fluoresces to produce a secondary light source 205 to illuminate a particle such as particle 206. Incident light 202 may be introduced in an out-of-plane direction of the slit in substrate 203. In some example embodiments, micropyramid 201 may focus light 202 into a narrow beam with beam width 3-4 microns, beam width 1-6 microns, beam width 5-20 microns, beam width 10-50 microns, beam width 30-80 microns, beam width 50-100 microns, and/or beam width 1-100 microns. Scattered light 204 may form a dark-field image of particles for biological analyte detection. Secondary light source 205 from autofluorescence of the lens material or micropyramid 201 forms a bright field image of particle 206 in a different region of the imager 207. Two correlated images, the dark field large-angle scattering image and bright-field transmissive image, may enable an image processing algorithms to eliminate false positive signals due to dust particles or debris thereby improving the detection sensitivity and accuracy. The disclosed technology provides for two correlated images on the same screen, in spite of the fact that the bright-field transmissive image is usually 5-6 orders of magnitude brighter than the large-angle scattered light. Without the disclosed technology, these two correlated images, dark field large-angle scattering image and bright-field transmissive image, cannot be formed on the same imager. In some example embodiments, semi-pyramid 220 in FIG. 2B may direct the incident light 208 at a predetermined angle based on the geometrical shape of micro pyramid 220.

In example embodiments, external lens 301 in FIG. 3 may be placed in front of imager 302 to form an image. An array of micro pyramids 303 may overlay slit layer 304 with multiple slits 304A. Incident light 305 may be deflected by the array of micro pyramids 303 and one or more particles may scatter light that is focused by lens 301 on imager 302.

Immunometric Binding Component

Figure 4A:
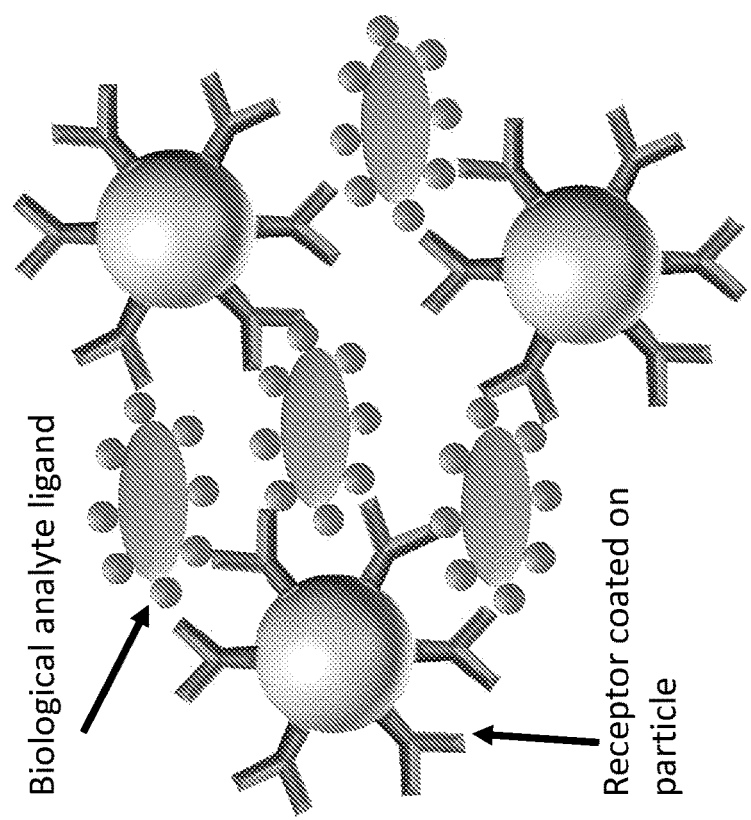
FIG. 4A illustrates an example reaction in a positive test for antigens, in accordance with some example embodiments.
Figure 4B:
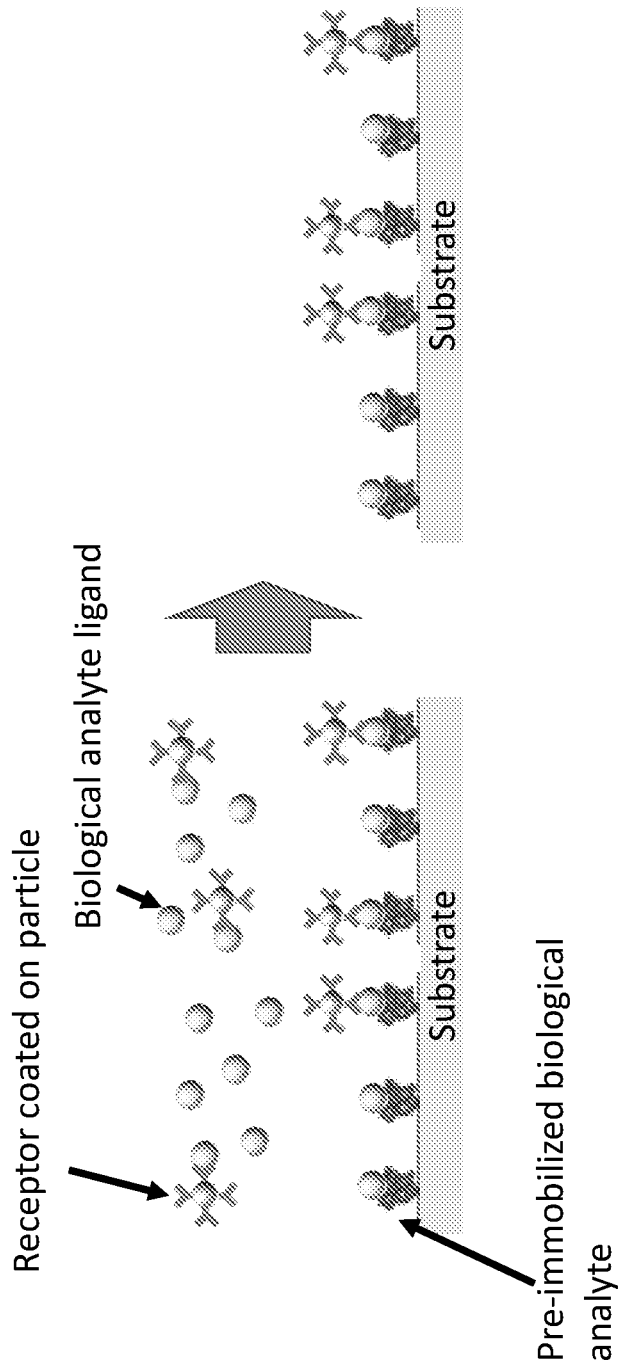
FIG. 4B illustrates an example immunoassay for narrow beam scanning, in accordance with some example embodiments.

The disclosed technology provides a detection means for detecting binding-member-specific binding pair member of analytes to be interacted with a binding mechanism such that the binding complex forms to connect particles and analytes, leading to scattered light for detection. Any binding pair member of analytes can be analyzed in the disclosed system when the specific binding reaction causes the effective interaction and detectable particle/analyte conjugate as shown in FIGS. 4A and 4B. For example, the polyclonal antibodies can be used to detect antigen in an immunoassay. The antibody-coated particles, which are available in a wide variety of materials including ceramics, glass, polymers and metal, may respond to form the particle agglutination including an in-vitro agglutination of particles mediated by specific reactions between antibodies immobilized on particles and antigens of analytes. To enhance the sensitivity and extend the point of equivalence, antibodies are immobilized on the surface of particles. When the fluid sample containing targeted analytes is introduced, the particle agglutination may take place as antibodies on the particles surface bind to antigens on the analyte surface. Via the specific antibody/antigen immunochemistry, the particle agglutination may offer a simple and nonhazardous method for fast and specific biological analyte detection. The sensitivity, specificity, and efficiency of detection are determined by factors such as uniformity of particle size and quality of the antibodies immobilized on the particles.

FIG. 4A illustrates an example reaction in a positive test for antigens, in accordance with some example embodiments; When particles are coated with specific binding member to bind with the binding pair member of analytes, particle agglutination develops because of the presence of binding pair member. Binding members on particles will not recognize those non-specific bind pair member, thus showing no agglutination effect unless the target receptors are present.

FIG. 4B illustrates an exemplary competitive immunoassay for narrow beam scanning. For the specific biological analyte detection, the same analytes are immobilized on the substrate. Test particles are coated with specific binding member to bind with the binding pair member of analytes. When the high levels of unknown analytes are present, the less test particles will be captured on the substrate, leading to the less accumulative scattered light collected under narrow beam scanning, in accordance with some example embodiments;

In another aspect, the specific carbohydrate sequences can be applied to detect biological analyte and their secreted toxins bin. For example, type-1 fimbriae are found on the majority of *Escherichia coli* (*E. coli*) strains allowing bacteria to colonize environmental surfaces or cells for infection of host cells. Type 1 fimbriae present on the surface of enterobacteriaceae may be responsible for mannose- and mannoside-binding activity as shown by binding chemistry of analytes to carbohydrates. For example, the mannose can use self-assembled mannose monolayer (SAM) fabrication for detection of *escherichia coli*. In the disclosed technology, carbohydrates, e.g. mannose, can be conjugated to silica particles to generate a multivalent carbohydrate moiety to amplify the response signal. When analytes are introduced, proteins on the membrane surface of analytes can bind with carbohydrate molecules, e.g. mannose. By doing so, the *E. coli*-mannose complex can be formed for the analyte detection.

Capillary-Driven Microfluidics

Figure 5:
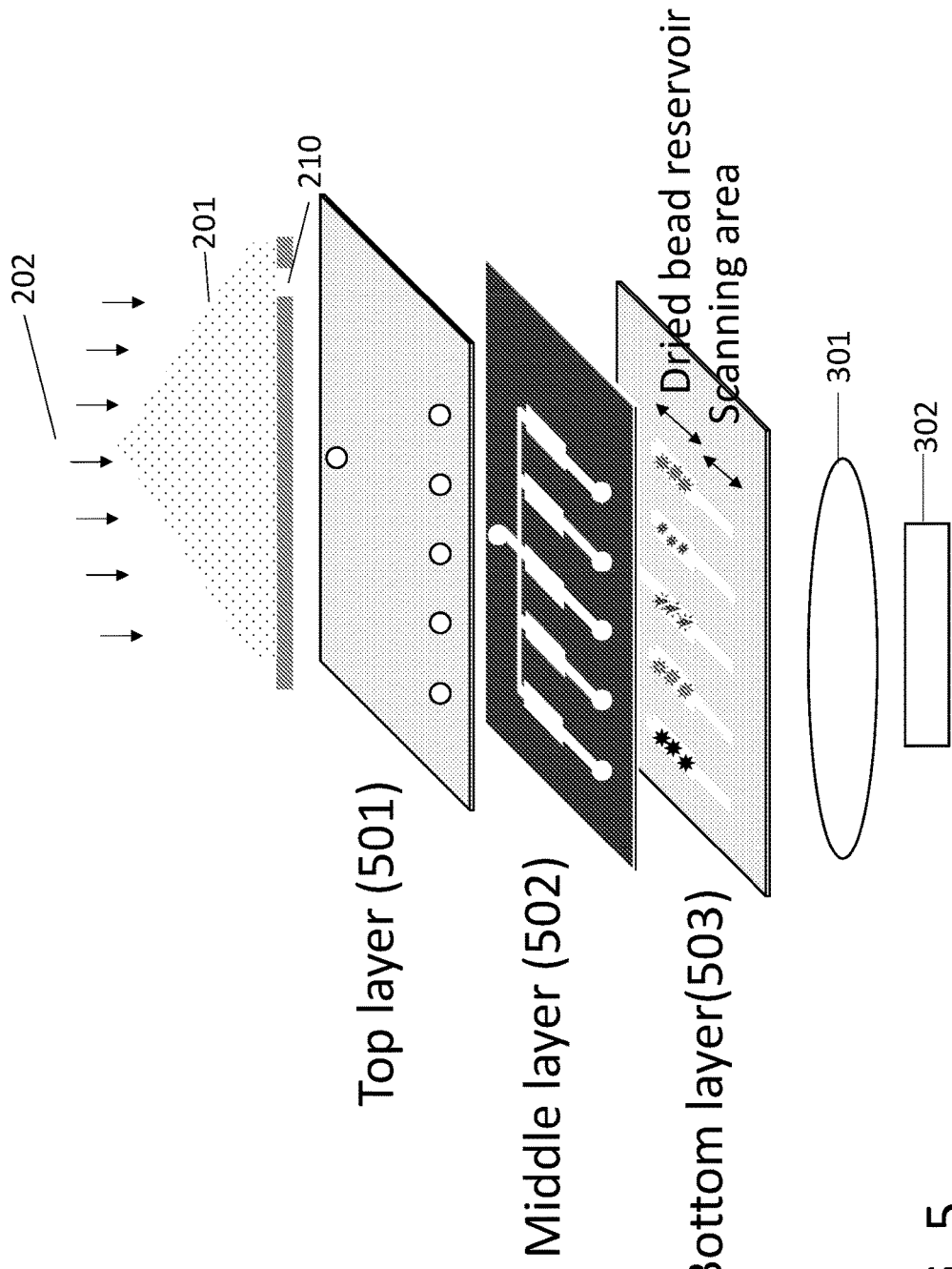
FIG. 5 illustrates an example of a capillary-driven microfluidic device for multiplexed detection, in accordance with some example embodiments.

Taking portability and ease of use into consideration, the disclosed technology offers capillary-driven microfluidic devices to execute rapid analyte detection on mobile electronics. In FIG. 5, a microfluidic device with dimensions of less than few hundred microns can include multiple layers. While not limited to those shown in FIG. 5, as an example only, FIG. 5 shows three layers, including: (1) top layer 501 that includes at least one sample introduction inlet and at least one outlet, (2) middle layer 502 that includes microfluidic channels, and (3) bottom layer 503 that includes a reservoir pattern wherein the ligand-receptor reaction can take place. When dispensing the sample containing analyte at the inlet, the capillary effect drives the liquid into the microfluidic channels. The binding pair member on a analyte can react with antibodies on the particle surface and bring the particles to the downstream channel for sensing. Depending on the analyte concentration levels, the degree of agglutination can vary and the intensity of a scattered light signal can indicate the biological analyte concentration. The disclosed design of microfluidic devices enables an accurate control of fluid transport.

In some example embodiments, the disclosed microfluidic devices may integrate with a dual-vision imaging system aforementioned on the top of sample introduction layer 501. When transporting fluid through microfluidic channels, the analyte within microfluidic channels layer 502 will be interrogated by the disclosed imaging technique. In another embodiment, the disclosed design of microfluidic devices may integrate with dual-vision imaging system aforementioned on the bottom of bottom layer 503. For example, micro pyramid 201 and layer 203 in FIG. 2A may be positioned above top layer 501 and imager 207 may be placed below bottom layer 503. When transporting fluid through microfluidic channels, the analyte within microfluidic channels layer 502 will be interrogated by the disclosed imaging technique.

Figure 6:
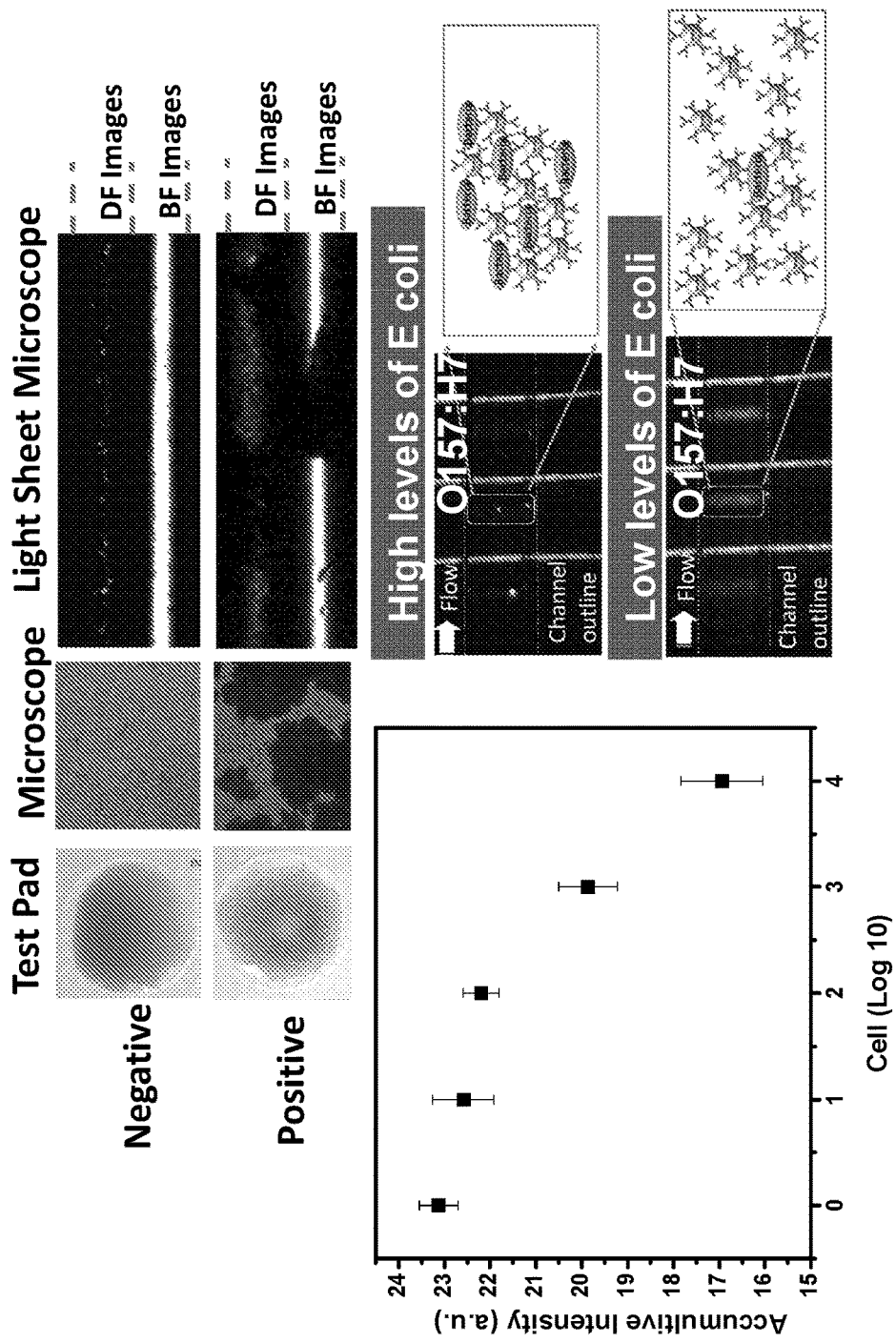
FIG. 6 illustrates an example of an agglutination test, in accordance with some example embodiments.

In some implementations, an *escherichia coli* O157:H7 antibody-coated kit (for example, Hardy Diagnostics) can be used to demonstrate the detection of analytes. FIG. 6 shows a drop of inactivated *escherichia coli* O157:H7 antigen suspension dispensed on pads for positive and negative tests. FIG. 6 shows an exemplary agglutination test indicating that when *escherichia coli* O 157:H7 is present, the particle agglutination effect will take place. In contrast, particle agglutination does not occur in non-*escherichia coli* O 157 suspension. Examples of agglutination pattern difference and a standard curve are shown for analysis. After introducing an inactivated *escherichia coli* O157:H7 antigen reagent, the particle agglutination on the test pads is shown within 90 seconds. Under an optical microscope, antibody coated particles reacted with *escherichia coli* O157:H7 antigen to form the agglutination in the positive test. In comparison, the particles without antibody coating show no sign of agglutination as negative control. Both samples are examined with dual-vision imaging system in the microchannels. Because of significant particle agglutination, the images of particle agglutination from a positive sample are shown as bright areas in the dark-field region. In contrast, the negative control sample shows a uniform, featureless field due to the absence of particle agglutination. The bright field transmissive image and the dark field scattering image can be simultaneously observed within the same field of view on the same imager. The bright-field images show clear contrasts for the positive sample and a featureless band for the negative sample, consistent with the observations under a conventional optical microscope. Furthermore, the positive sample show a much stronger speckle pattern in the dark-field scattering image than the negative sample. With such distinctive features for particle agglutination, the disclosed technology can yield unambiguous results for detection of targeted analytes. The disclosed technology can further quantify the *escherichia coli* O157:H7 cells. By recognizing agglutination pattern difference and accumulative scattering intensity, the high level of antigen will have greater agglutination and lower accumulative scattering intensity; on the contrary, antibody-coated beads have less chance to bind with antigen to form agglutination in the low level of antigen condition so under the narrow beam scanning each bead contributes scattered light to produce high accumulative scattering intensity across the dark field imaging band. The standard curve of *escherichia coli* O157:H7 in FIG. 6 clearly indicates the limit of detection can achieve 1~10 cells of *E coli*, which is sensitive to distinguish infectious dose of *escherichia coli* O157:H7 (>10 cells).

In some embodiment, the disclosed technology can be implemented to detect protein levels to demonstrate the feasibility of using the narrow beam scanning microscope and the immunoagglutination method for other enzyme or protein detection. A matrix metalloproteinase-8 (MMP8), which is involved in the pathogenesis of periodontitis diseases and plays an important role in infarction evolution as well as cardiac remodeling. The 0.6 μm polystyrene beads as MMP8-antibody carriers to avoid steric hindrance due to smaller size of MMP8. FIG. 7 shows an example agglutination test indicating that when matrix metalloproteinase-8 (MMP-8) is present, the particle agglutination degree will change based on the levels of present MMP-8. As shown, the significant scattered light intensity changes when increasing MMP8 protein levels, indicating that the limit of detection (LOD) could achieve 20 ng with a wide detection dynamic range. The standard curve can be tuned by the ratio of antibody to protein to achieve the most sensitive region under the linear Heidelberger-Kendall curve.

Figure 8:
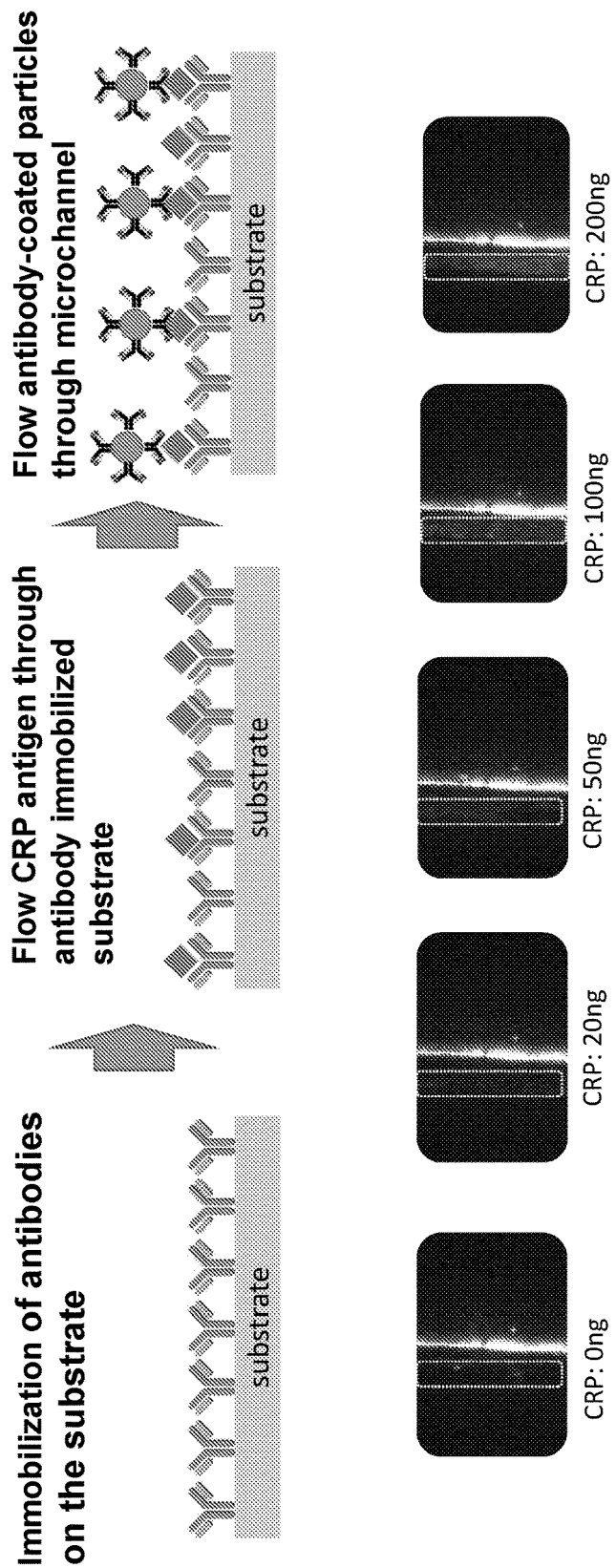
FIG. 8 illustrates an example of a sandwich immunoassay test, in accordance with some example embodiments.

In some implementations, a sandwich immunoassay is applied with the narrow beam scanning platform. The monoclonal antibodies of C-reactive protein (CRP), which is a biomarker for inflammation in the body, are immobilized onto the substrate, followed by flowing CRP antigen and antibody-coated particles. When unknown CRP levels in the sample is high, the more resulting captured particles will be observed on the substrate by scanning with the narrow beam. FIG. 8 shows the LOD of CRP that can be distinguished is 50 ng. FIG. 8 shows an exemplary sandwich immunoassay test indicating that the higher level of C-reactive protein (CRP) exists in a sample, the more scattered spots will be observed under narrow beam scanning.

In some implementations, parallel capillary-driven microfluidic channels can perpendicularly underlay a slit that make tilting light beam to enable a multiplexed detection at one time. Each microfluidic channel may load with the same or different ligand-coated particles for multi-sample detection using the same imager.

Figure 9:
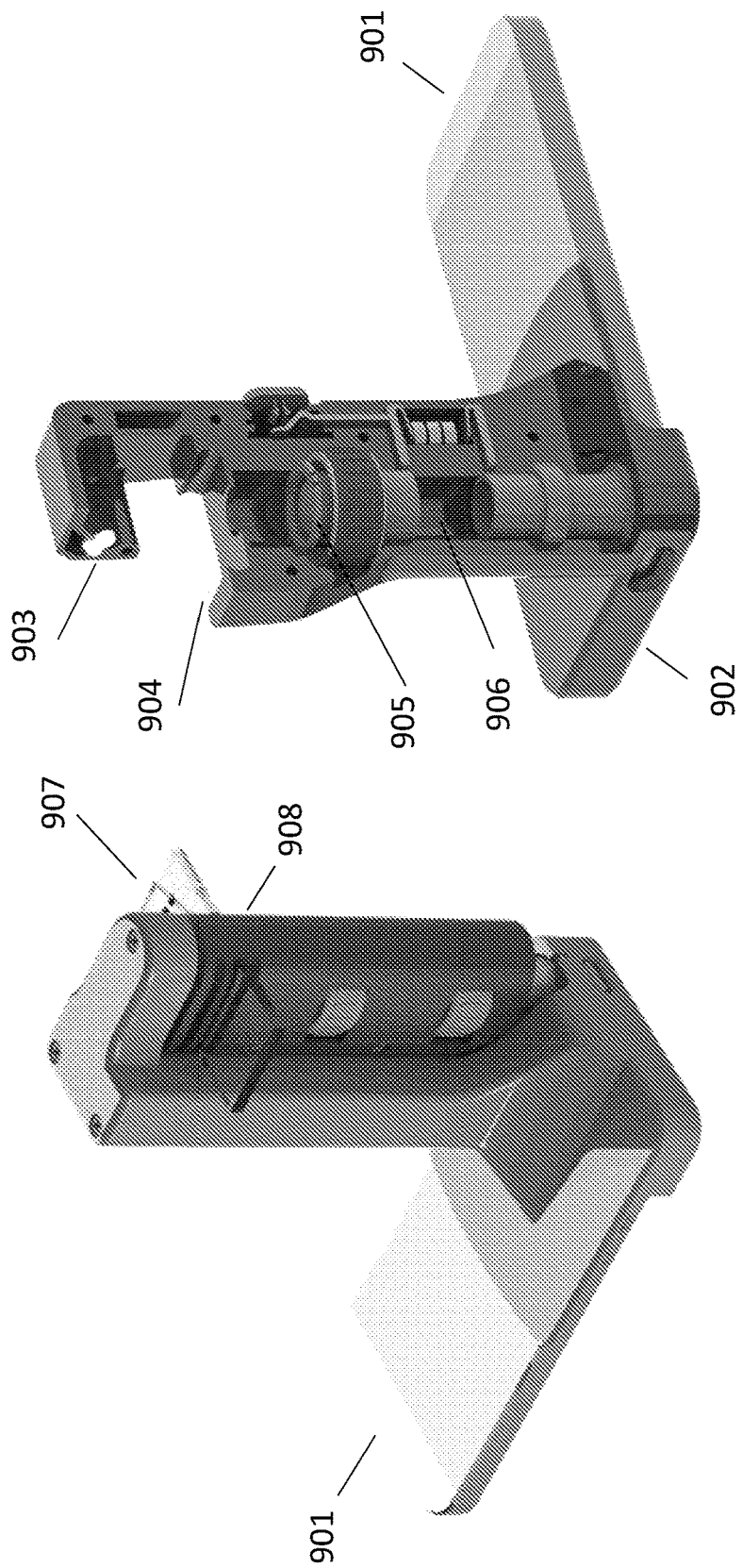
FIG. 9 illustrates an example of an apparatus, in accordance with some example embodiments.

Consistent with some example embodiments, FIG. 9 depicts the an example where a CMOS imager on a mobile device such as a smartphone is used as the imaging device for the bioimaging based on the dual-imaging approach disclosed herein. An adapter is provided to mechanically engage a bioimaging system based on FIGS. 1A-3 to Smartphone 901 (e.g. iPhone, Apple Inc.) and to optically the CMOS imaging sensor of the smartphone 901 to perform the dual-imaging operations for capturing the dark-field scattering light image and the bright-field fluorescent image. In the illustrated example, the smartphone 9-901 may be equipped with a CMOS imager that can be utilized to implement dual-vision imaging such as the foregoing dark-field imaging and bright-field imaging. The adapter includes a mechanical engagement unit to engage to the portion of the smartphone 901 in which the smartphone camera is located. Dongle 902 is provided to include a light source 903 (e.g. LED), a holder slot 904, and a lens 905 (e.g. 20× plastic lens) for imaging the microfluidic samples onto the CMOS imaging sensor in the smartphone 901. When placing smartphone 901 into dongle 902, the optical axis 906 will be self-aligned with a CMOS imager on smartphone 901. To execute detection, users may place a microfluidic device 907 that has beam narrowing structure and applicable immunometric assays onto sample slider 908. After introducing the fluid sample, the sample slider is inserted into the holder slot 904. The light source 903 can illuminate through the beam narrowing structure to produce a dual-vision imaging band. Executable instructions executed at smartphone 901 can cause recording of images received by the CMOS imager. In some example embodiments, image processing may be performed to determine the sizes and/or shapes of the scattered incident light and/or shadows. The adapter design shown in FIG. 9 can be used to couple an existing imaging sensor in a device other than a smart phone to perform the disclosed bioimaging. Examples of such other devices include a tablet with a camera module.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed:

1. A bioimaging apparatus, comprising:
a microfluidic holder that holds a microfluidic device to carry a fluid to be measured;
an optically opaque plate formed on a first side of the microfluidic holder and structured to include one or more slits to allow passage of light;
an illumination light source structure to produce, at a predetermined angle, illumination light towards the optically opaque plate to pass through one or more slits as a directional illumination beam to enter the microfluidic device to illuminate the fluid;
a fluorescent material placed adjacent to the optically opaque plate at a location to be illuminated by the illumination light to produce fluorescent light that passes through the one or more slits to enter the microfluidic device to illuminate the fluid; and
an image capture plate placed on a second side of the microfluidic holder and structured to block the illumination light that transmits through the microfluidic device at the predetermined angle and to include an imaging aperture that allows transmission of both (1) a portion of scattered light from the fluid caused by illumination of the fluid by the illumination light and (2) a portion of the fluorescent light that passes through the fluid which projects a shadow created by a particle in the fluid passing through the imaging aperture when illuminated by the fluorescent light.

2. The bioimaging apparatus of claim 1, wherein the microfluidic device includes one or more channels for receiving a sample fluid that includes target particles, wherein each channel includes an imaging region in the sample fluid to generate scattered light from target particles, wherein the target particles are illuminated by the incident light.

3. The bioimaging apparatus of claim 1, further includes an imaging device that is placed relative the image capture plate to receive, from the imaging aperture, (1) the portion of scattered light from the fluid caused by illumination of the fluid by the illumination light as a dark-field image and (2) the portion of the fluorescent light that passes through the fluid which projects a shadow created by a particle in the fluid passing through the imaging aperture when illuminated by the fluorescent light as a bright-field image.

4. The bioimaging apparatus of claim 1, wherein a horizontal distance between the one or more slits causes a predetermined width of the directional beam.

* * * * *